US006617132B2

(12) United States Patent
Ni et al.

(10) Patent No.: US 6,617,132 B2
(45) Date of Patent: *Sep. 9, 2003

(54) HUMAN CYSTATIN E POLYNUCLEOTIDES

(75) Inventors: Jian Ni, Germantown, MD (US); Reiner L. Gentz, Rockville, MD (US); Guo-Liang Yu, Berkeley, CA (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/940,497

(22) Filed: Aug. 29, 2001

(65) Prior Publication Data

US 2002/0052476 A1 May 2, 2002

Related U.S. Application Data

(60) Division of application No. 09/241,376, filed on Feb. 2, 1999, now Pat. No. 6,300,477, which is a division of application No. 08/744,138, filed on Nov. 5, 1996, now Pat. No. 6,011,012, which is a continuation-in-part of application No. 08/461,030, filed on Jun. 5, 1995, now Pat. No. 5,985,601.

(51) Int. Cl.[7] .......................... C12N 5/10; C12N 15/12; C12N 15/63

(52) U.S. Cl. .................... 435/69.1; 435/71.1; 435/71.2; 435/325; 435/320.1; 435/252.3; 435/254.11; 435/471; 536/23.5; 530/350

(58) Field of Search ................ 435/69.1, 71.1, 435/71.2, 252.3, 254.11, 325, 320.1, 471; 536/23.1, 23.5; 530/350

(56) References Cited

U.S. PATENT DOCUMENTS

| 5,212,297 A | | 5/1993 | Colella et al. |
| 5,432,264 A | | 7/1995 | Grubb et al. |
| 5,985,601 A | * | 11/1999 | Ni et al. .................... 435/69.1 |

FOREIGN PATENT DOCUMENTS

| EP | 0 373 771 | 6/1990 |
| WO | WO 88/09384 | 12/1988 |

OTHER PUBLICATIONS

Mikayama et al. Proc. Natl. Acad. Sci. USA. vol. 90, pp. 10056–10060, 1993.*
Voct et al. Biochemistry. John Wiley & Sons, Inc. pp. 126–128, and 228–236, 1990.*
Cole et al., "The cDNA structure and expression analysis of the genes for the cysteine proteinase inhibitor Cystatin C and for $\beta_2$-microglobulin in rat brain." *European Journal of Biochemistry*, 186:35–42 (1989).

Freiji et al., "Structure and expression of the gene encoding cystatin D, a novel human cysteine proteinase inhibitor." *Journal of Biological Chemistry*, 266(30):20538–20543 (1991).
Saitoh et al., "Human cysteine–proteinase inhibitors: nucleotide sequence analysis of three members of the cystatin gene family." *Gene*, 61:329–338 (1987).
Saitoh et al., "The human cystatin gene (CST3) is a member of the cystatin gene family which is localized in Chromosome 20." *Biochem. Biophys. Res. Comm.*, 162(3):1324–1331 (1989).
Pennacchio et al., "Mutations in the gene encoding Cystatin B in progressive myoclonus epilepsy (EPM1)." *Science*, 271:1731–1733 (1996).
Sotiropoulu et al., "Identification, cloning, and characterization of Cystatin M, a novel cysteine proteinase inhibitor, down–regulated in breast cancer." *Journal of Biological Chemistry*, 272(2):903–910 (1997).
Harlow et al., *Antibodies, A Laboratory Manual*. Cold Spring Harbor Laboratory, Ch. 5, p. 76 (1988).
Cunningham et al., "High–resolution epitope mapping of hGH–receptor interactions by alanine–scanning mutagenesis." *Science*, 244:1081–1085 (1989).
George et al., Macromolecular sequencing and synthesis. Alan R. Liss, Inc. N.Y. Ch. 12, pp. 127–149 (1988).
Esnard et al., "Two rat homologues of human Cystatin C." *FEBS Letters*, 236(2):475–478 (1988).
Ni et al., "Cystatin E is a novel human cysteine proteinase inhibitor with structural resemblance to family 2 cystatins." *Journal of Biological Chemistry*, 272(16):10853–10858 (1997).
Snow Brand Milk Product Co. Ltd., "Novel Cysteine Protease Inhibitor Inhibits Papain, Useful as Starting Material for Food or Pharmaceutical for Inhibiting Bone Ageing," WPI World Patent Information Derwent, GB, Derwent, 28(95), XP002031097 (abstract).
Supplementary European Search Report corresponding to European Application No. 95922973 (mailed Feb. 29, 2000).
Geneseq Accession No. AAW55826, "Cysteine protease inhibitor protein" (1998).
Geneseq Accession No. AAW15791, "Human cystein proteinase inhibitor Cystatin M" (1998).

(List continued on next page.)

*Primary Examiner*—Prema Mertz
(74) *Attorney, Agent, or Firm*—Human Genome Sciences, Inc.

(57) ABSTRACT

Disclosed is a human CysE polypeptide and DNA (RNA) encoding such polypeptide. Also provided is a procedure for producing such polypeptide by recombinant techniques. Also disclosed are methods for utilizing such polypeptide for treating osteoporosis, tumor metastases, microbial infections, viral infection, septic shock, inflammation, retinal irritation, caries, cachicia and muscle wasting. Diagnostic methods for detecting mutations in the coding sequence and alterations in the concentration of the polypeptides in a sample derived from a host are also disclosed.

69 Claims, 5 Drawing Sheets

OTHER PUBLICATIONS

Geneseq Accession No. AAV25967, "Cysteine proteinase inhibitor protein encoding cDNA" (1998).

Geneseq Accession No. AAT60608, "Human cysteine proteinase inhibitor Cystatin M cDNA" (1998).

GenBank Accession No. U62800, Sotiropoulou et al., "Homo sapiens cystatin M (CST6) mRNA, complete cds." (Aug. 24, 1996).

GenBank Accession No. AAB06566, "Cystatin M" (Aug. 23, 1996).

GenBank Accession No. W72895, "zd59h11.s1 Soares$_{13}$fetal$_{13}$heart$_{13}$NbHH19W Homo sapiens cDNA clone IMAGE:344997 3' similar to SW:CYT$_{13}$RAT P14841 Cystatin C Precursor;, mRNA sequence." (Oct. 16, 1996).

GenBank Accession No. N80906, "zb07c05.s1 Soares$_{13}$fetal$_{13}$lung$_{13}$NbHL19W Homo sapiens cDNA clone IMAGE:301352 3' similar to SW:CYT$_{13}$BITAR P08935 Cystatin. [1];, mRNA sequence." (Mar. 29, 1996).

GenBank Accession No. W68423, "zd36f07.s1 Soares$_{13}$fetal$_{13}$heart$_{13}$NbHH19W Homo sapiens cDNA clone IMAGE:342757 3' similar to SW:CYT$_{13}$BITAR P08935 Cystatin. [1];, mRNA sequence." (Oct. 15, 1996).

GenBank Accession No. W56781, "zd16e08.s1 Soares$_{13}$fetal$_{13}$heart$_{13}$NbHH19W Homo sapiens cDNA clone IMAGE:340838 3' similar to SW:CYT$_{13}$BITAR P08935 Cystatin. [1];, mRNA sequence." (Oct. 15, 1996).

GenBank Accession No. W74525, "zd74f10.s1 Soares$_{13}$fetal$_{13}$heart$_{13}$NbHH19W Homo sapiens cDNA clone IMAGE:346411 3' similar to SW:CYTC$_{13}$RAT P14841 Cystatin C Precursor;, mRNA sequence." (Oct. 17, 1996).

GenBank Accession No. AA041516, "zf10e07.r1 Soares$_{13}$fetal$_{13}$heart$_{13}$NbHH19W Homo sapiens cDNA clone IMAGE:376548 5' similar to SW:CYTC$_{13}$Mouse P21460 Cystatin C Precursor;, mRNA sequence." (Feb. 1, 1997).

Zeeuwen et al., "Cystatin M/E expression is restricted to differentiated epidermal keratinocytes and sweat glands; a new skin–specific proteinase inhibitor that is a target for cross–linking by transglutaminase." *Journal of Investigative Dermatology*, 116(5):693–710 (2001).

* cited by examiner

```
            10                    30                    50
CCGACGGCACTGACGGCCATGGCGCGTTCGAACCTCCCGCTGGCGCTGGGCCTGGCCCTG
                  M  A  R  S  N  L  P  L  A  L  G  L  A  L
            70                    90                    110
GTCGCATTCTGCCTCCTGGCGCTGCCACGCGATGCCCGGGCCCGGCCGCAGGAGCGCATG
 V  A  F  C  L  L  A  L  P  R  D  A  R  A  R  P  Q  E  R  M
           130                   150                   170
GTCGGAGAACTCCGGGACCTGTCGCCCGACGACCCGCAGGTGCAGAAGGCGGCGCAGGCG
 V  G  E  L  R  D  L  S  P  D  D  P  Q  V  Q  K  A  A  Q  A
           190                   210                   230
GCCGTGGCCAGCTACAACATGGGCAGCAACAGCATCTACTACTTCCGAGACACGCACATC
 A  V  A  S  Y  N  M  G  S  N  S  I  Y  Y  F  R  D  T  H  I
           250                   270                   290
ATCAAGGCGCAGAGCCAGCTGGTGGCCGGCATCAAGTACTTCCTGACGATGGAGATGGGG
 I  K  A  Q  S  Q  L  V  A  G  I  K  Y  F  L  T  M  E  M  G
           310                   330                   350
AGCACAGACTGCCGCAAGACCAGGGTCACTGGAGACCACGTCGACCTCACCACTTGCCCC
 S  T  D  C  R  K  T  R  V  T  G  D  H  V  D  L  T  T  C  P
           370                   390                   410
CTGGCAGCAGGGGCGCAGCAGGAGAAGCTGCGCTGTGACTTTGAGGTCCTTGTGGTTCCC
 L  A  A  G  A  Q  Q  E  K  L  R  C  D  F  E  V  L  V  V  P
           430                   450                   470
TGGCAGAACTCCTCTCAGCTCCTAAAGCACAACTGTGTGCAGATGTGATAAGTCCCCGAG
 W  Q  N  S  S  Q  L  L  K  H  N  C  V  Q  M  *
           490                   510                   530
GGCGAAGGCCATTGGGTTTGGGGCCATGGTGGAGGGCACTTCACGTCCGTGGGCCGTATC 550                   570
TGTCACAATAAATGGCCAGTGCTGCTTCTTGCAAAAAAAAAAAAAAAAA
```

FIG.1

```
  1  MARSNLPLALGLALVAFCLLALPRDARARPQ.ERMVGELRDLSPDDPQVQ   49
     || .  :  | ||::|..| . |  .:......  .|:||: .| |.::..|.
  1  MAGPLRAPLLLLAILAVALAVSPATGSSPGKPPRLVGGPMDASVEEEGVR   50

50  KAAQAAVASYNMGSNSIYYFRDTHIIKAQSQLVAGIKYFLTMEMGSTDCR   99
     :| : ||:.||..:||.:|. |. ::::|..|:|||:.|||.:|:|.|.|
 51  RALDFAVGEYNKASNDMYHSRALQVVRARKQIVAGVNYFLDVELGRTTCT   100

100  KTRVTGDHVDLTTCPLAAGAQ.QEKLRCDFEVLVVPWQNSSQLLKHNCVQ   148
     ||      :.:|..||: ..::  . | |.|:::..|||..  | | .|:
101  KT.....QPNLDNCPFHDQPHLKRKAFCSFQIYAVPWQGTMTLSKSTCQD   145

| | | |
|---|---|---|
| 1 | MAGPLRAPLLLLAILAVALAVSPAAGSSPGKPPRLVGGPM | Cystatin C |
| 1 | MMWPMHTPLLLLTALMVAVA------GSASAQSRTLAGGI | Cystatin D |
| 1 | MARSNLPLALGLALVAFCLLALPRDA-RARPQERMV-GEL | Cystatin E |
| 1 | MARPLCTLLLLMATLAGALASSSKEEN------RIIPGGI | Cystatin S |
| 1 | MAQHLSTLLLLLLATLAVALAWSPKEED------RIIPGGI | Cystatin SA |
| 1 | MAWPLCTLLLLLLATQAVALAWSPQEED------RIIEGGI | Cystatin SN |

| | | |
|---|---|---|
| 41 | -DASVEEEGVRRALDFAVGEYNKA-SNDMYHSRALQVVRA | Cystatin C |
| 35 | HATDLNDKSVQRALDFAISEYNKVINKDEYYSRPLQVMAA | Cystatin D |
| 39 | RDLSPDDPQVQKAAQAAVASYNMG-SNSIYYFRDTHIIKA | Cystatin E |
| 35 | YDADLNDEWVQRALHFAISEYNKA-TEDEYYRRPLQVLRA | Cystatin S |
| 35 | YNADLNDEWVQRALHFAISEYNKA-TKDDYYRRPLRVLRA | Cystatin SA |
| 35 | YDADLNDERVQRALHFVISEYNKA-TEDEYYRRLLRVLRA | Cystatin SN |

| | | |
|---|---|---|
| 79 | RKQIVAGVNYFLDVELGRTTCTKT-----QPNLDNCPFHD | Cystatin C |
| 75 | YQQIVGGVNYYFNVKFGRTTCTKS-----QPNLDNCPFND | Cystatin D |
| 78 | QSQLVAGIKYFLTMEMGSTDCRKTRVTGDHVDLTTCPLAA | Cystatin E |
| 74 | REQTAGGVNYFFDVEVGRTICTKS-----QPNLDTCAFHE | Cystatin S |
| 74 | RQQTVGGVNYFFDVEVGRTICTKS-----QPNLDTCAFHE | Cystatin SA |
| 74 | REQIVGGVNYFFDIEVGRTICTKS-----QPNLDTCAFHE | Cystatin SN |

| | | |
|---|---|---|
| 114 | QPHLKRKAFCSFQIYAVPWQGTMTLSKSTC-QDA | Cystatin C |
| 110 | QPKLKEEEFCSFQINEVPWEDKISILNYKC-RKV | Cystatin D |
| 118 | GAQ-QEKLRCDFEVLVVPWQNSSQLLKHNCVQM | Cystatin E |
| 109 | QPELQKKQLCSFEIYEVPWEDRMSLVNSRC-QEA | Cystatin S |
| 109 | QPELQKKQLCSFEIYEVPWENRRSLVKSRC-QES | Cystatin SA |
| 109 | QPELQKKQLCSFQIYEVPWEDRMSLVNSRC-QEA | Cystatin SN |

FIG.3

HUMAN CYSTATIN E POLYNUCLEOTIDES

CROSS REFERENCE TO RELATED APPLICATIONS

This application is a divisional of and claims priority under 35 U.S.C. §120 to U.S. application Ser. No. 09/241,376, filed Feb. 2, 1999 now U.S. Pat. No. 6,300,477, which is a divisional of and claims priority under 35 U.S.C. §120 to U.S. application Ser. No. 08/744,138, filed Nov. 5, 1996 (now U.S. Pat. No. 6,011,012, issued on Jan. 4, 2000), which is a continuation-in-part of and claims priority under 35 U.S.C. §120 to U.S. application Ser. No. 08/461,030, filed Jun. 5, 1995 (now U.S. Pat. No. 5,985,601, issued on Nov. 16, 1999), all of which are hereby incorporated by reference in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as human cystatin E, sometimes hereinafter referred to as "CysE". The invention also relates to inhibiting the action of such polypeptides.

BACKGROUND OF THE INVENTION

The cystatin superfamily comprises a group of cysteine proteinase inhibitors which are widely distributed in human tissues and body fluids, and which form tight and reversible complexes with cysteine proteinases such as cathepsins B, H, L, and S. The cystatins are most likely involved in the regulation of normal or pathological processes in which these proteinases participate. Thus, cystatins may influence the intra- and extracellular catabolism of proteins and peptides (Barret, A. J. and Kirchke, H., Methods Enzymol., 80:535–561 (1981)), regulate proteolytic processing of pro-hormones (Orlowski, M., Mol. Cell. Biochem., 52:49–74 (1983)) and pro-enzymes (Taugner, R., et al., Histochemistry, 83:103–108 (1985)), protect against penetration of normal tissues by malignant cells (Sloane, B. F., Semin. Cancer Biol., 1:137–152 (1990)) or microorganisms (Bjorck, L., et al., Nature, 337:385–386 (1989) and Bjorck, L., et al., J. Virol., 64:941–943 (1990)) and modulate local inflammatory processes in rheumatoid arthritis (Mort, J. S., et al., Arthritis Rheum., 27:509–515 (1984)) and purulent bronchiectasis (Buttle, D. J., et al., Scand. J. Clin. Lab. Invest., 50:509–516 (1990)).

The cystatin superfamily has been sub-divided into families I, II and III (also called the stefin, cystatin and kininogen families, respectively), each with members differing from those of the other families in structural organization and biological distribution (Barret, A. J., et al., Biochem. J., 236:312 (1986)). The family I cystatins A and B are small proteins consisting of single polypeptide chains of about 100 amino acid residues without disulfide bridges. The family II cystatins consist of polypeptide chains of approximately 120 amino acid residues with two intra-chain disulfide bonds. Finally, the family III cystatins, the kininogens, display a higher degree of structural complexity characterized by the presence of three family II cystatin-like domains, each with two disulfide bridges at positions homologous to those in family II cystatins (Muller-Esterl, W., et al., Transbiochem. Sci., 11:336–339 (1986)). Family I and II cystatins are mainly present intracellularly and in secretory fluids (Abrahamson, M., et al., J. Biol. Chem., 261:11282–11289 (1986)), whereas kininogens are highly concentrated in blood plasma (Adam, A., et al., Clin. Chem., 31:423–426 (1985)).

At least one type II cystatin, designated cystatin C, appears to be expressed in all tissues (Abrahamson, M., et al., Biochem. J., 268:287–294 (1990)). In contrast, S-type cystatins are found predominantly in saliva (Abrahamson, M., et al., J. Biol. Chem., 261:11282–11289 (1986)). Cystatins and derivative peptides possess antibacterial and antiviral activities (Bjorck, et al. (1989, 1990)), consistent with their presence in secretions bathing epithelial surfaces directly exposed to the environment. The cystatins may also modulate the immune response. This could occur directly, by inhibiting cysteine protease releases by macrophages (Bieth, J., Cysteine Proteinases and Their Inhibitors, V. Turk, ed. (Walter De Gruyter & Company, New York) pp. 693–703 (1986)), or indirectly, by inhibiting the chemotaxic response and the phagocytosis-associated respiratory burst of the cells (Leung-Tack, et al., Biol. Chem., 371:255–258 (1990)). This data suggests that type II cystatins might perform a variety of protective functions at epithelial surfaces. The human type II cystatin gene family consists of at least seven members.

The disease hereditary cystatin C amyloid angiopathy (HCCAA) is associated with a Glu to Leu mutation in the gene encoding cystatin C. This leads to deposition of amyloid fibrils comprised of this mutant cystatin C in the cerebral arteries, which appears to cause fatal hemorrhaging (Ghiso, J., et al., PNAS, USA, 83:2974–2978 (1986)).

The polypeptide of the present invention has been putatively identified as a CysE as a result of amino acid sequence homology to cystatin C and on conservation of cystatin-like functional motifs in its amino acid sequence.

SUMMARY OF THE INVENTION

The present invention provides isolated nucleic acid molecules comprising a polynucleotide encoding the CysE polypeptide having the amino acid sequence shown in FIG. 1 (SEQ ID NO:2) or the amino acid sequence encoded by the cDNA clone deposited with the American Type Culture Collection (ATCC®, located at 10801 University Boulevard, Manassas, Va. 20120-2209, USA) in a bacterial host as ATCC® Deposit Number 97156 on May 22, 1995. The nucleotide sequence determined by sequencing the deposited CysE clone, which is shown in FIG. 1 (SEQ ID NO:1), contains an open reading frame encoding a polypeptide of 149 amino acid residues, with a leader sequence of about 28 amino acid residues, and a predicted molecular weight of about 14 kDa. The amino acid sequence of the mature CysE protein is shown in FIG. 1, amino acid residues 29–149 (SEQ ID NO:2).

Thus, one aspect of the invention provides an isolated nucleic acid molecule comprising a polynucleotide having a nucleotide sequence selected from the group consisting of: (a) a nucleotide sequence encoding the CysE polypeptide having the complete amino acid sequence in FIG. 1 (SEQ ID NO:2); (b) a nucleotide sequence encoding the mature CysE polypeptide having the amino acid sequence at positions 29–149 in FIG. 1 (SEQ ID NO:2); (c) a nucleotide sequence encoding the CysE polypeptide having the complete amino acid sequence encoded by the cDNA clone contained in ATCC® Deposit No. 97156; (d) a nucleotide sequence encoding the mature CysE polypeptide having the amino acid sequence encoded by the cDNA clone contained in ATCC® Deposit No. 97156; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CysE polypeptide having an amino acid sequence in (a), (b), (c) or (d), above.

The present invention also relates to recombinant vectors, which include the isolated nucleic acid molecules of the present invention, and to host cells containing the recombinant vectors, as well as to methods of making such vectors and host cells and for using them for production of CysE polypeptides or peptides by recombinant techniques.

The invention further provides an isolated CysE polypeptide having an amino acid sequence selected from the group consisting of: (a) the amino acid sequence of the CysE polypeptide having the complete 149 amino acid sequence, including the leader sequence shown in FIG. 1 (SEQ ID NO:2); (b) the amino acid sequence of the mature CysE polypeptide (without the leader) having the amino acid sequence at positions 29–149 in FIG. 1 (SEQ ID NO:2); (c) the amino acid sequence of the CysE polypeptide having the complete amino acid sequence, including the leader, encoded by the cDNA clone contained in ATCC® Deposit No. 97156; and (d) the amino acid sequence of the mature CysE polypeptide having the amino acid sequence encoded by the cDNA clone contained in ATCC® Deposit No. 97156. The polypeptides of the present invention also include polypeptides having an amino acid sequence with at least 90% similarity, and more preferably at least 95% similarity to those described in (a), (b), (c) or (d) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a CysE polypeptide having an amino acid sequence described in (a), (b), (c) or (d), above. Peptides or polypeptides having the amino acid sequence of an epitope-bearing portion of a CysE polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a CysE polypeptide having an amino acid sequence described in (a), (b), (c) or (d) above.

The invention further provides methods for isolating antibodies that bind specifically to a CysE polypeptide having an amino acid sequence as described herein. Such antibodies are useful diagnostically or therapeutically as described below.

The present invention also provides a screening method for identifying compounds capable of enhancing or inhibiting modulation of proteinase activity by CysE, which involves contacting CysE with a proteinase in the presence of the candidate compound, assaying the ability of the proteinase to cleave a substrate in the presence of CysE and the candidate compound, and comparing the result with a standard, the standard being assayed when contact is made in absence of the candidate compound; whereby, an increased in substrate cleavage over the standard indicates that the compound is an agonist and a decreased substrate cleavage over the standard indicates that the compound is an antagonist.

In another aspect, a screening assay for agonists and antagonists is provided which involves determining the effect a candidate compound has on CysE binding to a CysE binding molecule. In particular, the method involves contacting a CysE binding molecule with a CysE polypeptide and a candidate compound and determining whether CysE polypeptide binding to the CysE binding molecule is increased or decreased due to the presence of the candidate compound.

The present inventors have discovered that CysE is expressed in amniotic cell, fetal skin and placental tissues. For a number of disorders related to fetal development, it is believed that significantly higher or lower levels of CysE gene expression can be detected in affected tissues taken from an individual having, or carrying a child having, such a disorder, relative to a "standard" CysE gene expression level, i.e., the CysE expression level in healthy tissue from an individual not having, or carrying a child not having the fetal development disorder. Thus, the invention provides a diagnostic method useful during diagnosis of disorders, such as fetal development disorders, which involves: (a) assaying CysE gene expression level in cells or body fluid of an individual; (b) comparing the CysE gene expression level with a standard CysE gene expression level, whereby an increase or decrease in the assayed CysE gene expression level compared to the standard expression level is indicative of the disorder.

An additional aspect of the invention is related to a method for treating an individual in need of an increased level of CysE activity in the body comprising administering to such an individual a composition comprising a therapeutically effective amount of an isolated CysE polypeptide of the invention or an agonist thereof.

A still further aspect of the invention is related to a method for treating an individual in need of a decreased level of CysE activity in the body comprising, administering to such an individual a composition comprising a therapeutically effective amount of a CysE antagonist. Preferred antagonists for use in the present invention are CysE-specific antibodies.

BRIEF DESCRIPTION OF THE FIGURES

FIG. 1 illustrates the cDNA (SEQ ID NO:1) and corresponding deduced amino acid sequence (SEQ ID NO:2) of CysE. The protein has a leader sequence of about 28 amino acid residues (underlined) and a deduced molecular weight of about 14 kDa. The predicted amino acid sequence of the mature CysE protein is also shown. The standard one-letter abbreviation for amino acids is used.

FIG. 2 shows an alignment of the amino acid sequences of Cystatin E (upper line) (SEQ ID NO:2) and Cystatin C (lower line) (SEQ ID NO:3) indicating regions of identity and similarity.

FIG. 3 shows the regions of identity between the amino acid sequence of the CysE protein and other human cystatins: cystatin C (SEQ ID NO:3); cystatin D (SEQ ID NO:4); cystatin S (SEQ ID NO:5); cystatin SN; (SEQ ID NO:6); and cystatin SA (SEQ ID NO:7).

FIG. 4b shows a phylogenetic tree alignment prepared using the similarity score data shown in FIG. 4a.

DETAILED DESCRIPTION OF THE INVENTION

Figure 4A:
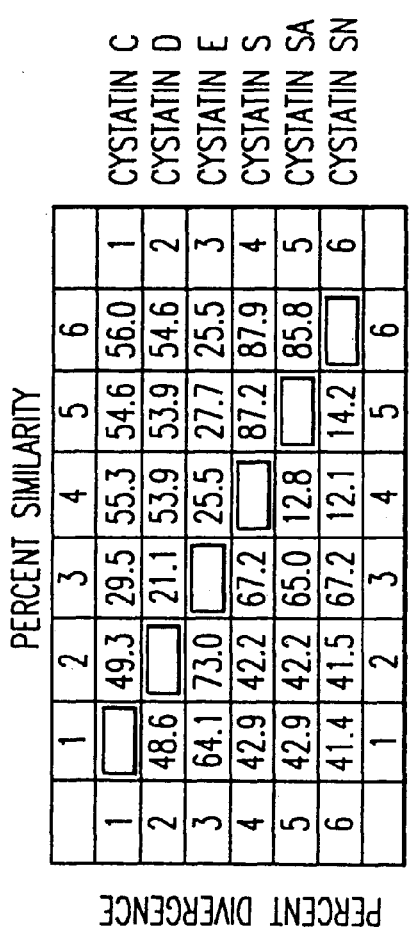
FIG. 4a shows a percent similarity score in tabular fashion of the human cystatins shown in FIG. 3 using the Clustal method with PAM250 residue weight table.
Figure 4B:
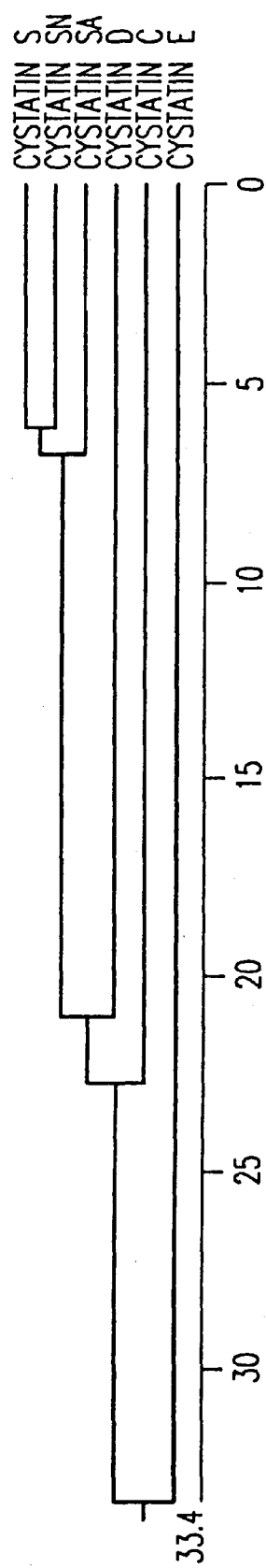
Figure 5:
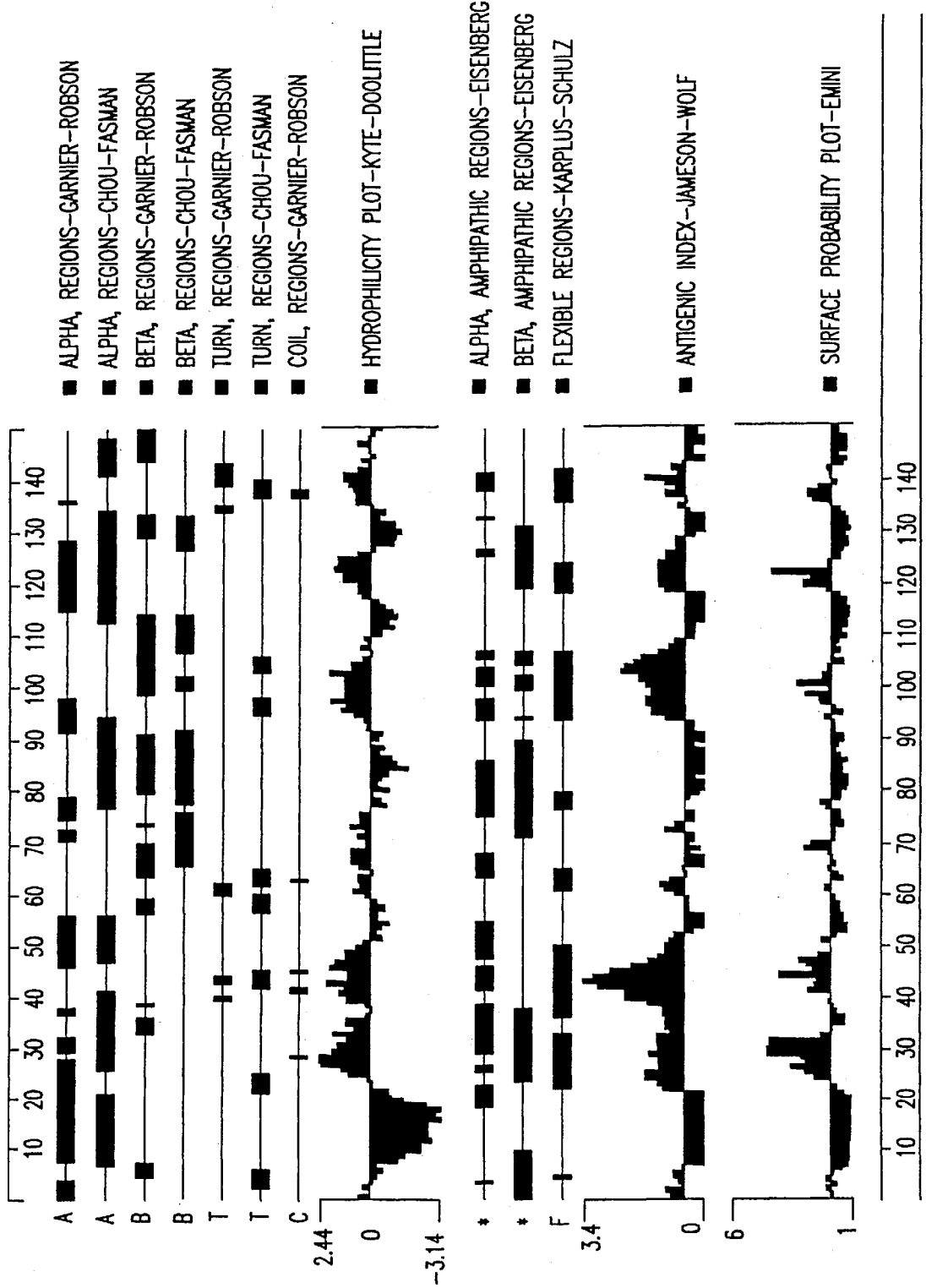
FIG. 5 shows an analysis of the CysE amino acid sequence. Alpha, beta, turn and coil regions; hydrophilicity and hydrophobicity; amphipathic regions; flexible regions; antigenic index and surface probability are shown. In the "Antigenic Index—Jameson—Wolf" graph, amino acid residues Ala 26-Gln 53; Met 93-His 107; Gly 118-Phe 128; and Gln 136-Gln 148 in FIG. 1 correspond to the shown highly antigenic regions of the CysE protein.

In accordance with an aspect of the present invention, there is provided an isolated nucleic acid (polynucleotide) which encodes for the CysE polypeptide having the deduced amino acid sequence of FIG. 1 (SEQ ID NO:2) or for the mature polypeptide encoded by the cDNA of the clone HAQBM60 (SEQ ID NO:1) deposited as ATCC® Deposit No. 97156 on May 22, 1995. This cDNA was isolated from a cDNA library derived from primary culture amniotic cells.

The CysE polypeptide is structurally related to the cystatin II superfamily. The cDNA clone encoding CysE contains an open reading frame encoding a 149 residue preprotein (FIG. 1; SEQ ID NO:1), of which the first 28 amino acids likely constitute the signal peptide according to an alignment with human cystatin sequences (FIG. 2). This indicates a closer relationship with the secreted Family 2 cystatins than with the intracellular Family 1 cystatins. The open reading frame contains a typical consensus sequence for initiation of translation (Kozak, M., J. Mol. Biol., 196:947–950 (1987)) around the start ATG codon, and was followed by a poly(A) signal, AATAAA, 78 nt downstream from the stop codon, after which a poly(A) sequence was evident further 20 nt downstream (not shown).

The deduced mature protein sequence was just 34% identical to that of cystatin C, showed lower resemblance (26–30% identity) to the sequences of the other known Family 2 cystatins D, S, SN and SA (FIGS. 2 and 3), and even lower similarities of 20 and 22% identical residues when compared to the Family 1 cystatins, A and B (not shown). However, the sequence contains a Gly residue at exactly the same distance from a central Gln-Xaa-Val-Xaa-Gly motif as the other cystatin sequences, and also a Pro-Trp pair towards the C-terminal end of the translation product, like that of the human Family 2 cystatins. The sequence also contains 4 Cys residues towards the C-terminal end, alignable with those in Family 2 cystatins. The four Cys residues in cystatin C and the avian analogue, chicken cystatin, form two disulfide bridges stabilizing the cystatin structure (Grubb et al., *FEBS Lett.*, 170:370–74 (1984); Bode et al., *EMBO J.*, 7:2593–99 (1988)). The novel protein was thus similar to Family 2 cystatins in parts essential for structure and function, and was designated cystatin E. Its evolutionary relationship to the cystatin superfamily seems indisputable, but according to the relatively low sequence similarities it should be seen as a first member in a new protein family (Dayhoff, et al., In: Dayhoff, MO., ed., *Atlas of Protein Sequence and Structure*, National Biomedical Research Foundation, Washington, Vol. 5, Suppl. 3, pp. 9–20 (1979)).

The cystatin E sequence also has some unusual characteristics, including a 5 residue insertion between amino acids 76 and 77 and a deletion of residue 91 (cystatin C numbering). These sequence positions correspond to polypeptide parts on the side opposite to the proteinase binding region of chicken cystatin (Bode et al., 1988, supra), and would likely not affect an inhibitory function of cystatin E. A motif search in addition showed a target Asn-Xaa-Ser/Thr sequence for glycosylation at positions 137–139 (SEQ ID NO:2). On the gene level, a cystatin multigene locus on the short arm of chromosome 20 has been investigated in detail. This locus harbors the genes for the known Family 2 cystatins C, D, S, SN and SA, and in addition two pseudogenes, but according to estimates using cross-hybridizing probes in Southern blotting, likely no additional genes (Abrahamson et al., *Biochem. J.*, 268:287–294 (1990), Schnittger et al., *Genomics*, 16:50–55 (1993), Thiesse et al., *DNA Cell Biol.*, 13:97–116 (1994)). Again, this supports that cystatin E is a protein distantly, but significantly, related to the Family 2 cystatins.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding a CysE polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from primary culture amniotic cells.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the CysE polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the full-length CysE polypeptide having the complete amino acid sequence in FIG. 1 (SEQ ID NO:2), including the predicted leader sequence; (b) a nucleotide sequence encoding the mature CysE polypeptide (full-length polypeptide with the leader removed) having the amino acid sequence at positions 29–149 in FIG. 1 (SEQ ID NO:2); (c) a nucleotide sequence encoding the full-length CysE polypeptide having the complete amino acid sequence including the leader encoded by the cDNA clone contained in ATCC® Deposit No. 97156 (d) a nucleotide sequence encoding the mature CysE polypeptide having the amino acid sequence encoded by the cDNA clone contained in ATCC® Deposit No. 97156; or (e) a nucleotide sequence complementary to any of the nucleotide sequences in (a), (b), (c) or (d).

By a polynucleotide having a nucleotide sequence at least, for example, 95% "identical" to a reference nucleotide sequence encoding a CysE polypeptide is intended that the nucleotide sequence of the polynucleotide is identical to the reference sequence except that the polynucleotide sequence may include up to five point mutations per each 100 nucleotides of the reference nucleotide sequence encoding the CysE polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having CysE activity. This is because even where a particular nucleic acid molecule does not encode a polypeptide having CysE activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CysE activity include, inter alia, (1) isolating the CysE gene or allelic variants thereof in a cDNA library; (2) in situ hybridization (e.g., "FISH") to metaphase chromosomal spreads to provide precise chromosomal location of the CysE gene, as described in Verma et al., Human Chromosomes: A Manual of Basic Techniques, Pergamon Press, New York (1988); and (3) Northern Blot analysis for detecting CysE mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having CysE protein activity. By "a polypeptide having CysE activity" is intended polypeptides exhibiting activity similar, but not necessarily identical, to an activity of the CysE protein of the invention (either the full-length protein or, preferably, the mature protein), as measured in a particular biological assay. For example, the CysE protein of the present invention acts as a cysteine protease inhibitor by inhibiting papain and cathepsin activity. A preferred papain inhibiting assay is described in Example 10 below.

CysE protein modulates papain activity in a dose-dependent manner in the assay described in Example 10. Thus, "a polypeptide having CysE protein activity" includes polypeptides that also exhibit any of the same papain modulating activities in the above-described assay in a dose-dependent manner. Although the degree of dose-dependent activity need not be identical to that of the CysE protein, preferably, "a polypeptide having CysE protein activity" will exhibit substantially similar dose-dependence in a given activity as compared to the CysE protein (i.e., the candidate polypeptide will exhibit greater activity or not more than about tenfold less and, preferably, not more than about twofold less activity relative to the reference CysE protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having CysE protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CysE protein activity. This is because the skilled artisan is fully aware of amino acid substitutions that are either less likely or not likely to significantly effect protein function (e.g., replacing one aliphatic amino acid with a second aliphatic amino acid).

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

For example, guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Leader Sequence and Mature CysE

The polynucleotide which encodes the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

More particularly, the present invention also provides the mature form(s) of the CysE protein. According to the signal hypothesis, proteins secreted by mammalian cells have signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CysE polypeptide having the amino acid sequence encoded by the cDNA clone contained in the host identified as ATCC® Deposit 97156. By the mature CysE polypeptide having the amino acid sequence encoded by the cDNA in ATCC® Deposit No. 97156 is meant the mature form(s) of the CysE protein produced by expression in a mammalian cell (e.g., COS cells, as described below) of the complete open reading frame encoded by the human DNA sequence of the clone contained in the deposit.

In addition, methods of predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (Virus Res. 3:271–286 (1985)) uses the information from a short N-terminal charged region and a subsequent uncharged region of the complete (uncleaved) protein. The method of von Heinje (Nucleic Acids Res. 14:4683–4690 (1986)) uses the information from the residues surrounding the cleavage site, typically residues –13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for any given protein.

In the present case, the predicted amino acid sequence of the complete CysE polypeptide was analyzed by a computer program "PSORT", available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted a cleavage site between amino acids 28 and 29 of the amino acid sequence shown in FIG. 2 (SEQ ID NO:2). Thus, the leader sequence for the CysE protein is predicted to consist of amino acid residues 1–28 of SEQ ID NO:2, while the predicted mature protein consists of residues 29–149 of SEQ ID NO:2.

In order to experimentally confirm the N-terminal sequence of the mature secreted CysE polypeptide the cystatin E cDNA, ATCC® Deposit 97156, was subcloned in a baculovirus expression vector and was expressed in Sf9 insect cells according to the method of Example 2. The recombinantly produced protein was secreted into the cell media of such cultures, with a yield of approximately 10 to 20 mg/l culture medium. The secreted protein was purified according to the method of Example 5. Briefly, the protein was subjected to a combination of ion exchange and dye affinity column chromatographies, resulting in a greater than 95% pure protein preparation according to SDS/PAGE, provided that the observed protein band doublet was due to microheterogeneity of the same protein.

N-terminal sequence analysis was determined by automated Edman Degredation using a model ABI-494 sequencer according to the method of Example 6, but could have been determined by other techniques well known in the art. N-terminal sequence analysis of both protein bands confirmed that the observed protein doublet was not due to alternative leader cleavage products as each species began with amino acid 29 (Arg) of SEQ ID NO:2. The N-terminal Arg residue corresponds with residue 4 in the cystatin C sequence and agrees with a theoretical signal peptidase cleavage site as discussed above. Subsequent studies with the N-linked oligosaccharide cleaving enzyme PNGase, as described in Example 9 below, showed that the observed microheterogeneity was due to the presence of a glycosylated form of CysE.

As one of ordinary skill would appreciate from the above discussion, due to the possibility of sequencing errors as well as the variability of cleavage sites in different known proteins, the predicted and experimentally confirmed mature CysE polypeptide(s) encoded by the deposited cDNA consists of about 121 amino acids (presumably residues 29–149 of SEQ ID NO:2), but may consist of any number of amino acids in the range of about 109 to 134; and the actual leader sequence(s) of this protein is expected to be 28 amino acids (presumably residues 1–28 of SEQ ID NO:2, but may consist of any number of amino acids in the range of about 15 to 40.

In addition, it is known in the art that for many proteins, including the mature form(s) of a secreted protein, that one or more amino acids may be deleted from the N-terminus without substantial loss of biological function (CysE activity). For instance, for many proteins, including the mature form(s) of a secreted protein, it is known in the art that one or more amino acids may be deleted from the N-terminus without substantial loss of biological function. In the present case, since the protein of the invention is a member of the cystatin polypeptide family, deletions of N-terminal amino acids up to the Val 35 of the Arg-Met-Val-Gly motif (which corresponds with the Arg-Leu-Val-Gly motif in Cystatin C), may retain CysE activity. Polypeptides having further N-terminal deletions including the Val 35 residue would not be expected to retain such biological activities because it is known that the valine in this motif interacts with the S2 substrate pocket of target enzymes (Bode et al., *EMBO J.*, 7:2593–99 (1988); Hall et al., *Biochem. J.*, 291:123–29 (1993)). However, even if deletion of one or more amino acids from the N-terminus of a protein results in modification of loss of one or more biological functions of the protein, other biological activities may still be retained. Thus, the ability of shortened protein to induce binding to and/or bind to antibodies which recognize the complete mature protein generally will be retained when less than the majority of the residues of the complete or mature protein are removed from the N-terminus. For example, immunological activity was retained by N-terminally truncated forms of CysE obtained from human urine, discussed below. Whether a particular polypeptide lacking N-terminal residues of a complete protein retains such immunologic activities can readily be determined by routine methods described herein and otherwise known in the art, for example, see Example 10.

Accordingly, the present invention further provides polypeptides having one or more residues deleted from the amino terminus of the amino acid sequence of CysE (SEQ ID NO:2), up to residue Val 35 of SEQ ID NO:2, and polynucleotides encoding such polypeptides. In particular, the present invention provides polypeptides having the amino acid sequence of amino acids n-149 of SEQ ID NO:2, where n is any integer 1–35. More in particular, the invention provides polypeptides having the amino acid sequence of residues 1–149, 2–149, 3–149, 4–149, 5–149, 6–149, 7–149, 8–149, 9–149, 10–149, 11–149, 12–149, 13–149, 14–149, 15–149, 16–149, 17–149, 18–149, 19–149, 20–149, 21–149, 22–149, 23–149, 24–149, 25–149, 26–149, 27–149, 28–149, 29–149, 30–149, 31–149, 32–149, 33–149, 34–149, and 35–149. Polynucleotides encoding these polypeptides also are provided.

Fragments, Analogs and Derivatives

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

Preferred nucleic acid fragments of the present invention include nucleic acid molecules encoding epitope-bearing portions of the CysE protein. In particular, such nucleic acid fragments of the present invention include nucleic acid molecules encoding: a polypeptide comprising amino acid residues from about Ala 26 to about Gln 53 in FIG. 1 (SEQ ID NO:2); a polypeptide comprising amino acid residues from about Met 93 to about His 107 in FIG. 1 (SEQ ID NO:2); a polypeptide comprising amino acid residues from about Gly 118 to about Phe 128 in FIG. 1 (SEQ ID NO:2); and a polypeptide comprising amino acid residues from about Gln 136 to about Gln 148 in FIG. 1 (SEQ ID NO:2). The inventor has determined that the above polypeptide fragments are antigenic regions of the CysE protein. Methods for determining other such epitope-bearing portions of the CysE protein are described in detail below.

It is known in the art that for many proteins, including the mature form(s) of a secreted protein, that one or more amino acids may be deleted from the C-terminus without substantial loss of biological function (CysE activity). The present inventors have discovered that a C-terminal deletion of up to at least six amino acids retains biological function. A DNA encoding a polypeptide having the amino acid sequence corresponding to amino acids 29–143 was amplified by PCR and cloned into a pA2 expression vector, according to the method of Example 2, except that a modified 3' primer was used which has the sequence 5'-CGCGGATCCTCACATCTGCAAAAAGTTGGCTT-3' (SEQ ID NO:8). The expression product has the amino acid sequence corresponding to amino acids 29–143 of SEQ ID NO:2 plus a 27 amino acid C-terminal fusion product encoded by the pA2 vector and having the sequence NH2-PTFCRCEDPTRESRKDLRYRSRHDKIHCOOH (SEQ ID NO:9). This mutant CysE is sometimes referred to herein as "m-CysE."

To test the function of CysE and m-CysE as protease inhibitors their effect on papain hydrolysis of casein was investigated according to the method of Example 10. Both CysE and m-CysE showed a dose- and time-dependent inhibition of papain activity (data not shown). At mM concentrations, the recombinant CysE completely inhibited papain hydrolysis of Bz-Arg-pNA in 10 minute assays (Example 10). Titration curves drawn from the results of the assays with varying inhibitor concentrations were linear, thus compatible with a reversible inhibition with Ki<10 nM. The active concentration preparation studied was 27 nM; that determined by quantitative amino acid analysis 40 mM, thus demonstrating that the CysE was close to 100% active. The apparently lower active concentration is most likely due to binding of the cystatin also to a papain species not capable of hydrolyzing the substrate, as has been shown to be the case for cystatin C in similar experiments (Abrahamson et al., 1988; Lindahl et al., 1990). The m-CysE mutant performed similarly (data not shown).

Certainly, as experimentally determined herein, amino acids from 144 to the C-terminus of CysE (SEQ ID NO:2) do not appear to be critical for retention of biological activity. For instance, for many proteins, including the mature form(s) of a secreted protein, it is known in the art that one or more amino acids may be deleted from the C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. However, even if deletion of one or more amino acids from the C-terminus of a protein results in modification of loss of one or more biological functions of the protein, other biological activities may still be retained. Thus, the ability of shortened protein to induce binding to and/or bind to antibodies which recognize the complete or mature protein generally will be retained when less than the majority of the residues of the complete or mature protein are removed from the C-terminus. Whether a particular polypeptide lacking C-terminal residues of a complete or mature protein retains such immunologic activities can readily be determined by routine methods described herein and otherwise known in the art.

Accordingly, the present invention further provides polypeptides having one or more residues from the carboxyl terminus of the amino acid sequence of CysE (SEQ ID NO:2), up to residue 143, and polynucleotides encoding such polypeptides. In particular, the present invention provides polypeptides having the amino acid sequence described by the formula n-c. Such formula describes polypeptides beginning with residue n where n is any of the residues 1–35 of the amino acid sequence in SEQ ID NO:2, and ending with amino acid c where c is any of the residues 143–149 of the amino acid of SEQ ID NO:2. Polypeptides of this range have been shown to possess biological activity herein. Polynucleotides encoding these polypeptides also are provided.

Hybridization Probes and PCR Primers

Fragments of the full length CysE gene may also be used as a hybridization probe, for example, for a cDNA library to isolate the full length CysE gene and to isolate other genes which have a high sequence similarity to the CysE gene or similar biological activity. Probes of this type preferably have at least 30 bases and may contain, for example, 50 or more bases. The probe may also be used to identify a cDNA clone corresponding to a full length transcript and a genomic clone or clones that contain the complete CysE gene including regulatory and promoter regions, exons, and introns. An example of a screen comprises isolating the coding region of the CysE gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

To investigate the tissue distribution of CysE, Northern blot experiments using radioactively labeled CysE cDNA, as shown in FIG. 1 (SEQ ID NO:1), as a probe were performed. The relatively low nucleotide sequence similarity with Family 2 cystatin cDNAs make it unlikely that the CysE probe would cross-hybridize with other cystatin mRNAs. In control experiments under similar stringency hybridization conditions there were no significant cross-reactions with cDNAs for cystatin C and D (data not shown). The indication from the Northern blot results are that the CysE gene is expressed in most tissue. However, the distribution pattern consisted of relatively strong mRNA signals in uterus and liver, and slightly weaker but significant signals in placenta, pancreas, heart, spleen, small intestine and peripheral blood leukocytes. This combined with the fact that most all of the cDNA clones identified originated either from amniotic cell or fetal skin libraries indicates that the CysE gene expression might be upregulated in the fetus and, thus, that the inhibitor could serve a protective role during fetal development.

The present invention relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. By "stringent conditions" is more particularly intended overnight incubation at 42° C. in a solution comprising: 50% formamide, 5×SSC (750 mM NaCl, 15 mM trisodium citrate); 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s) as measured by the assay described in Example 10, "Cys E activity."

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer. Several PCR primers, for example, are described and used throughout the Examples.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

CysE Polypeptides

The present invention further relates to a CysE polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide encoded by the deposited cDNA including the leader, the mature polypeptide encoded by the deposited cDNA minus the leader (i.e., the mature protein), the polypeptide of FIG. 1 (SEQ ID NO:2) including the leader, the polypeptide of FIG. 1 (SEQ ID NO:2) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of a CysE polypeptide is intended that the amino acid sequence of the polypeptide is identical to the reference sequence except that the polypeptide sequence may include up to five amino acid alterations per each 100 amino acids of the reference amino acid of the CysE polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. As known in the art "similarity" between two polypeptides is determined by comparing the amino acid sequence and its conserved amino acid substitutes of one polypeptide to the sequence of a second polypeptide. By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptide of the present invention could be used as a molecular weight marker on SDS-PAGE gels or on molecular sieve gel filtration columns using methods well known to those of skill in the art. In accordance with this aspect of the invention, the inventors have determined the mobility of the unglycosylated mature recombinant CysE polypeptide secreted from insect cells after reduction to correspond to approximately 14,000 daltons. This is in good agreement with the theoretical mass of CysE which is 13,652 daltons.

As described in detail below, and in Example 7, the polypeptides of the present invention can also be used to raise polyclonal and monoclonal antibodies, which are useful in assays for the detection of CysE protein expression, for purification of CysE, or as antagonists and agonists capable of enhancing or inhibiting CysE protein function. Further, such CysE polypeptides can be used in the yeast two-hybrid system to "capture" CysE protein binding proteins which are also candidate agonist and antagonists according to the present invention. The yeast two hybrid system is described in Fields and Song, *Nature*, 340:245–46 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein is generally less than the number of antigenic epitopes. See, for instance, Geysen, et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See, for instance, Sutcliffe, J. G., et al., *Science*, 219:660–66 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate CysE-specific antibodies include: a polypeptide comprising amino acid residues from about Ala 26 to about Gln 53 in FIG. 1 (SEQ ID NO:2); a polypeptide comprising amino acid residues from about Met 93 to about His 107 in FIG. 1 (SEQ ID NO:2); a polypeptide comprising amino acid residues from about Gly 118 to about Phe 128 in FIG. 1 (SEQ ID NO:2); and a polypeptide comprising amino acid residues from about Gln 136 to about Gln 148 in FIG. 1 (SEQ ID NO:2). As indicated above, the inventor has determined that the above polypeptide fragments are antigenic regions of the CysE protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to a carrier using a linker such as m-maleimidobenzoyl-N-hydroxysuccinimide ester (MBS), while other peptides may be coupled to a carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1 C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, CysE polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86 (1988)). Fusion proteins that have a disulfide-linked dimeric structure due to the IgG part can also be more efficient in binding and neutralizing other molecules than the monomeric CysE protein or protein fragment alone (Fountoulakis et al., *J. Biochem.* 270:3958–3964 (1995)).

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the CysE genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK+ or −, pBS(KS)+ or −, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC® 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Host cells expressing recombinant CysE are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Isolation of CysE Polypeptides

The polypeptide of the present invention can be recovered and purified from recombinant cell cultures by methods known to those of skill in the art including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

In order to isolate native CysE protein from a human source an antiserum was raised against the baculovirus expressed recombinant CysE produced according to the method of Example 2. The method used to raise the antiserum and isolate the IgG fraction are found in Example 7, below. Other methods of antiserum production and fractionation are standard in the art.

Urine from a patient with mixed glomerular-tubular proteinuria, a body fluid enriched in low-Mw proteins originating from blood plasma and previously shown to be a good source of cystatins (Abrahamson et al., J. Biol. Chem., 261:11282–89 (1986)), was obtained. Other sources of CysE could also be used, including for example, uterus, liver, placenta, pancreas, heart, spleen, small intestine, peripheral blood leukocytes, brain, testis and kidney tissues. Preferred are uterine and liver tissue. Particularly preferred is urine from a patient with mixed glomerular-tubular proteinuria.

The urine was concentrated and purified on an immunoaffinity column according to the method of Example 8. Briefly, the urine source of CysE was concentrated by pressure ultrafiltration. This step is optional but will increase overall yield when utilized. The resulting solution was applied to column packed with MiniLeak™ immunoaffinity resin having the IgG antiserum preparation coupled thereto. While MiniLea™ resin was used as a solid phase reagent herein, it will be readily apparent to those of ordinary skill in the art that many other materials may be used as solid phase reagents, for example, other polymeric resins, filter material, and polymeric beads to name a few. The attachment methods generally include non-specific adsorption of the protein to the support or covalent attachment of the protein, typically through a free amine group, such as an activated carboxyl, hydroxyl, or aldehyde group.

The column was extensively washed with Tris buffer. A glycine buffer was used to elute the purified CysE. Other purification techniques, known to those of skill in the art, could have been used including, ammonium sulfate or ethanol precipitation, acid extraction, anion or cation exchange chromatography, phosphocellulose chromatography, hydrophobic interaction chromatography, hydroxylapatite chromatography and lectin chromatography. Furthermore, protein refolding steps can be used, as necessary, in completing configuration of the mature protein. Finally, high performance liquid chromatography (HPLC) can be employed for final purification steps.

Subsequently the N-terminal sequence of the purified human CysE was determined by Edman degradation, according to the method of Example 6, and found to correspond with the sequence in FIG. 1 beginning with the methionine at amino acid position 34 in SEQ ID NO:2. The reason for the shorter N-terminal segment for the protein from human urine is likely due to the processing by bacterial proteases in the urine, agreeing with the presence of N-terminally truncated forms of other cystatins, e.g., cystatin C, in such urines ((Abrahamson et al.,*J. Biol. Chem.*, 261:11282–89 (1986)).

Accordingly, provided herein is a method of purifying native CysE from human tissue and body fluid. In one embodiment the method comprises the steps of: (a) obtaining a source of human CysE, (b) separating CysE from other components contained in the source of human CysE, and (c) collecting purified CysE.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polypeptides of the present invention are preferably provided in an isolated form, and preferably are substantially purified. A recombinantly produced version of the CysE polypeptide can be substantially purified by the method describe above, and more in particular in Example 5, below.

Treatment Methods

The CysE polypeptide of the present invention may be employed to inhibit human cathepsin enzymes and the resulting pathologies related to the action of these cathepsins. For example, CysE may be employed to treat osteoporosis, behcet disease, hypercalcemia, osteomalicia, allergic skin diseases, allergic rhinitis and allergic purpura.

It is also thought that the cathepsins play a vital role in the metastasizing of tumors and, accordingly, CysE may be employed to prevent tumor metastases.

The CysE polypeptide may be employed as an antimicrobial agent to halt the growth of certain microbial agents, for example, streptococci and to reduce dental caries by reducing the production of acids which contribute to caries.

The CysE polypeptide may also be employed as an antiviral agent to treat infection caused by viruses, for example, to prevent the replication of herpes simplex virus (HSV). The CysE polypeptide may also be employed to protect the retina against attack by the cystein proteinases.

The CysE polypeptide of the present invention may also be employed to treat cachexia and muscle wasting by preventing the action of cysteine proteinases.

The CysE polypeptide may also be employed as a protective agent during fetal development.

The CysE polypeptide may also be employed to modify inflammation, for example, that associated with rheumatoid arthritis, and to treat septic shock. The CysE polypeptide may also be employed to treat purulent bronchiectasis.

The CysE polypeptide may also be used to treat progressive inherited myoclonus epilepsy of the Unverricht-Lundborg type (Pennacchio, et al., Science, 271:1731–33 (1996)) and hereditary cystatin C amaloid angiopathy which causes fatal hemorrhaging, and may be associated with Alzheimer's disease, Down's syndrome, Parkinson's, and dementia.

The polynucleotides and polypeptides of the present invention may be employed as research reagents and materials for discovery of treatments and diagnostics to human disease.

Cystatin E Binding Molecules

This invention provides a method for identification of protein binding molecules for the cystatin E polypeptide. The gene encoding a cell-bound binding molecule can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the cystatin E polypeptide, and a cDNA library created from this RNA is divided into pools and used to transfect COS cells or other cells that are not responsive to the cystatin E polypeptide. Transfected cells which are grown on glass slides are exposed to labeled cystatin E polypeptide. The cystatin E polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and re-screening process, eventually yielding a single clone that encodes the putative binding molecule. As an alternative approach for binding molecule identification, labeled ligand can be photoaffinity linked with cell membrane or extract preparations that express the binding molecule. Cross-linked material is resolved by PAGE and exposed to X-ray film. The labeled complex containing the ligand-binding molecule can be excised, resolved into peptide fragments, and subjected to protein microsequencing. The amino acid sequence obtained from microsequencing would be used to design a set of degenerate oligonucleotide probes to screen a cDNA library to identify the gene encoding the putative membrane-bound binding molecule.

This invention provides a method of screening compounds to identify those which bind to the cystatin E membrane-bound binding molecule and induce a second messenger response therefrom. As an example, a mammalian cell or membrane preparation expressing the cystatin E binding molecule is incubated in the presence of the compound to be screened. The response of a known second messenger system following interaction of the compound and the binding molecule is measured and compared to the second messenger response induced by cystatin E. Such second messenger systems include but are not limited to, cAMP guanylate cyclase, ion channels or phosphoinositide hydrolysis.

Agonists and Antagonists

The polypeptide of the present invention and agonist compounds may be assayed for an ability to inhibit cysteine proteinase activity which assay comprises determining equilibrium constants for dissociation ($K_i$) of cystatin E complexes with papain and human cathepsin B, by continuous rate assays with 10 M Z-Phe-Arg-NHMec as substrate in 100 M sodium phosphate buffer (Nicklin, M. J. H., and Barrett, A. J., *Biochem. J.*, 223:245–253 (1984) or as described in Example 10. The buffer contains 1 mM dithiothreitol and 2 mM EDTA and is adjusted to pH 6.5 for papain assay and to pH 6.0 for cathepsin B assays. Cathepsin B is preincubated for 20 min in assay buffer at room temperature before use. The enzyme concentrations in the assays are 0.05–0.25 nM. The highest cystatin E concentration tried in cathepsin B assays is 100 nM. The inhibitor concentrations giving informative inhibition, i.e., resulting in a new steady state rate within 1 hour after addition of inhibitor, are 20–50 nM in the papain assays. Substrate hydrolysis at 37° C. is monitored in a Perkin-Elmer Cetus LS50 fluorometer at excitation and emission wavelengths of 360 and 460 nm, respectively. $K_m$ values for hydrolysis of Z-Phe-Arg-NHMec under the assay are used to compensate obtained apparent $K_i$ values for substrate induced dissociation of inhibitor, by the relationship: Apparent $K_i=K_i(1+[S]/K_m)$.

The polypeptides of the present invention and agonist compounds may be employed in combination with a suitable pharmaceutical carrier. Such compositions comprise a therapeutically effective amount of the polypeptide or agonist, and a pharmaceutically acceptable carrier or excipient. Such a carrier includes but is not limited to saline, buffered saline, dextrose, water, glycerol, ethanol, and combinations thereof. The formulation should suit the mode of administration.

CysE Pharmaceutical Compositions

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or agonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 g/kg body weight and in most cases they will be administered in an amount not in excess of about 8 mg/Kg body weight per day. In most cases, the dosage is from about 10 g/kg to about 1 mg/kg body weight daily, taking into account the routes of administration, symptoms, etc.

Gene Therapy

The CysE polypeptides and agonist compounds which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Diagnostics

The disease hereditary cystatin C amaloid angiopathy causes fatal hemorrhaging, and may be associated with Alzheimer's disease, Down's syndrome, Parkinson's, dementia, and could lead to death before age 40.

The disease progressive myoclonus epilepsy of the Unverricht-Lundborg type is caused by decreased expression and mutant forms of cystatin B.

This invention, therefore, relates to the use of the CysE gene as a diagnostic. Detection of a mutated form of CysE will allow a diagnosis of a disease similar to HCCAA and inherited epilepsy which results from a mutation in, or decreased expression of, the CysE gene.

Individuals carrying mutations in the human CysE gene may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., *Nature*, 324:163–166 (1986)) prior to analysis. RNA or cDNA may also be used for the same purpose. As an example, PCR primers complementary to the nucleic acid encoding CysE can be used to identify and analyze CysE mutations. For example, deletions and insertions can be detected by a change in size of the amplified product in comparison to the normal genotype. Point mutations can be identified by hybridizing amplified DNA to radiolabeled CysE RNA or alternatively, radiolabeled CysE antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., *PNAS, USA*, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present inventor has further discovered that CysE is expressed in amniotic cell, fetal skin and placental tissues. For a number of disorders related to fetal development, it is believed that significantly higher or lower levels of CysE gene expression can be detected in tissues, preferably amniotic tissue, taken from an individual having, or carrying a child having, such a disorder, relative to a "standard" CysE gene expression level, i.e., the CysE expression level in healthy tissue from an individual not having, or carrying a child not having the fetal development disorder. Thus, the invention provides a diagnostic method useful during diagnosis of CysE related disorders, including fetal development disorders and inherited epilepsy, which involves: (a) assaying CysE gene expression levels in cells or body fluid of an individual; (b) comparing the CysE gene expression level with a standard CysE gene expression level, whereby an increase or decrease in the assayed CysE gene expression level compared to the standard expression level is indicative of the disorder.

Chromosomal Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

CysE Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman, for example, according to the method of Example 7. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

EXAMPLES

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

The following examples are meant to illustrate particular aspects of the invention and are in no way intended as limiting.

Example 1

Bacterial Expression and Purification of Soluble CysE

The DNA sequence encoding CysE, ATCC® No. 97156, is initially amplified using PCR oligonucleotide primers corresponding to the 5' sequences of the mature CysE protein (minus the signal peptide sequence) and the vector sequences 3' to the CysE gene. Additional nucleotides corresponding to CysE are added to the 5' and 3' sequences respectively. The 5' oligonucleotide primer has the sequence

5' CGCCCATGGCCCGGCCGCAGGAGCGC 3'    (SEQ ID NO:10)

containing an NcoI restriction enzyme site (bold), followed by CysE coding sequence starting from the presumed terminal amino acid of the mature protein. The 3' oligonucleotide primer has the sequence

5' CGCAAGCTTGAATGGCCTTCGCCCTC 3'    (SEQ ID NO:11)

containing complementary sequences to a HindIII site (bold), and is followed by CysE coding sequence. The restriction enzyme sites correspond to the restriction enzyme sites on the bacterial expression vector pQE60 (Qiagen, Inc. Chatsworth, Calif., 91311). pQE60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE60 was then digested with NcoI and HindIII. The amplified sequences are ligated into pQE60 and are inserted in frame with the sequence encoding for the histidine tag and the RBS. The ligation mixture is then used to transform E.

coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 µg/ml) and Kan (25 µg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized CysE is purified from this solution by chromatography on a Nickel-Chelate column under conditions that allow for tight binding by proteins containing the 6-His tag (Hochuli, E. et al., *J. Chromatography* 411:177–184 (1984)). CysE is eluted from the column in 6 molar guanidine HCl pH 5.0 and for the purpose of renaturation adjusted to 3 molar guanidine HCl, 100 mM sodium phosphate, 10 molar glutathione (reduced) and 2 mmolar glutathione (oxidized). After incubation in this solution for 12 hours the protein is dialyzed to 10 mmolar sodium phosphate.

Example 2

Cloning and Expression of CysE using the Baculovirus Expression System

The DNA sequence encoding the full length CysE protein, ATCC® No. 97156, is amplified using PCR oligonucleotide primers corresponding to the 5' and 3' sequences of the gene:

The 5' primer has the sequence

```
                                         (SEQ ID NO:12)
5' CGCGGATCCGCCATCATGGCGCGTTCGAACCTC 3'
``` and contains a BamHI restriction enzyme site (in bold) followed by an efficient signal for the initiation of translation in eukaryotic cells (Kozak, M., *J. Mol. Biol.*, 196:947–950 (1987)) and 18 nucleotides of the CysE gene (the initiation codon for translation "ATG" is underlined).

The 3' primer has the sequence

```
5' CGCGGTACCGAATGGCCTTCGCCCTC 3'    (SEQ ID NO:13)
``` and contains the cleavage site for the restriction endonuclease Asp718 and nucleotides complementary to the 3' non-translated sequence of the CysE gene. The amplified sequences are isolated from a 1% agarose gel using a commercially available kit ("Geneclean," BIO 101 Inc., La Jolla, Calif.). The fragment is then digested with the endonuclease BamHI and Asp718 and then purified again on a 1% agarose gel.

The vector pA2 (modification of pVL941 vector, discussed below) is used for the expression of the CysE protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2, such as pRG1 pAc373, pVL941 and pAcIM1 (Luckow, V. A. and Summers, M. D., *Virology*, 170:31–39).

The plasmid is digested with the restriction enzyme BanHI and Asp718 and then dephosphorylated using calf intestinal phosphatase by procedures known in the art. The DNA is then isolated from a 1% agarose gel using the commercially available kit ("Geneclean" BIO 101 Inc., La Jolla, Calif.).

The fragment and dephosphorylated plasmid are ligated with T4 DNA ligase. *E. coli* HB101 cells are then transformed and bacteria identified that contained the plasmid (pBacCysE) with the CysE gene using the enzymes BamHI and Asp718. The sequence of the cloned fragment is confirmed by DNA sequencing.

5 µg of the plasmid pBacCysE was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacCysE are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to the Sf9 insect cells (ATCC® CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-CysE at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labeled proteins visualized by SDS-PAGE and autoradiography.

Example 3

Expression of Recombinant CysE in Mammalian Cells

Most of the vectors used for the transient expression of the CysE protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146) and pBC12MI (ATCC® 67109). Mammalian host cells that could be used include, human Hela, 283, H9 and Jurkart cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3. intron, the polyadenylation and termination signal of the rat preproinsulin gene.

Example 3(a)

Cloning and Expression in COS Cells

The expression plasmid, pCysE HA, is made by cloning a cDNA encoding CysE into the expression vector pcDNAI/Amp (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the CysE protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The CysE cDNA of the deposited clone is amplified using primers that contain convenient restriction sites, much as described above regarding the construction of expression vectors for expression of CysE in E. coli. To facilitate detection, purification and characterization of the expressed CysE, one of the primers contains a hemagglutinin tag ("HA tag") as described above.

Suitable primers include the following, which are used in this example. The 5' primer, containing the BamHI site (in bold), has the following sequence:

```
                                        (SEQ ID NO:12)
   5' CGCGGATCCGCATCATGGCGCGTTCGAACCTC 3'.
```

The 3' primer, containing the Asp718 site (in bold), has the following sequence:

```
   5' CGCGGTACCGAATGGCCTTCGCCCTC 3'.   (SEQ ID NO:13)
```

The PCR amplified DNA fragment and the vector, pcDNAI/Amp, are digested with BamHI and Asp718 and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the CysE-encoding fragment.

For expression of recombinant CysE, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y.

(1989). Cells are incubated under conditions for expression of CysE by the vector.

Expression of the CysE HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of CysE protein. Plasmid pC4 is a derivative of the plasmid pSV2-dhfr (ATCC® Accession No. 37146) The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., Molecular and Cellular Biology, March 1985:438–447) plus a fragment isolated from the enhancer of the immediate early gene of human cytomegalovirus (CMV) (Boshart et al., Cell 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the CysE in a regulated way in mammalian cells (Gossen, M., & Bujard, H. 1992, Proc. Natl. Acad. Sci. USA 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphates by procedures known in the art. The vector is then isolated from a 1% agarose gel.

The DNA sequence encoding the complete CysE protein including its leader sequence is amplified using PCR oligonucleotide primers corresponding to the 5' and 3' sequences of the gene. The 5' primer has the sequence (SEQ ID NO:12)
5' CGCGGATCCGCCATCATGGCGCGTTCGAACCTC 3' containing the BamHI restriction enzyme site (in bold) followed by an efficient signal for initiation of translation in eukaryotes, as described by Kozak, M., J. Mol. Biol. 196:947–950 (1987). The 3' primer has the sequence

5' CGCGGTACCGAATGGCCTTCGCCCTC 3'   (SEQ ID NO:13)

containing the underlined Asp718 restriction site.

The amplified fragment is digested with the endonucleases BamHI and Asp718 and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

Example 5

Purification of Recombinant Cystatin E

Recombinant cystatin E was purified from baculovirus infected Sf9 cell supernatants. All purification steps were carried out at 40° C., utilizing a BioCAD 250 (PerSeptive Biosystems, Inc.). Five-hundred ml of supernatant was first adjusted to pH 4.5 and then applied at a flow rate of 20 ml/min to a 10 ml Poros HS column pre-equilibrated with 100 mM NaOAc buffer, pH 4.5. The cystatin E was found in the flow-through fraction. After adjusting the pH of the CysE containing fraction to 8.5, the fraction was applied at a flow rate of 20 ml/min to a 10 ml Poros HQ column pre-equilibrated in 20 mM Tris-HCl buffer, pH 8.5. Cystatin E was again collected in the flow-through fraction. Finally, cystatin E was captured on a Mimetic Green 1 A6XL Alpha column (10 ml; ProMetic BioSciences, Inc., Burtonsville, Md.) pre-equilibrated with 25 mM sodium phosphate buffer, pH 6.0. After washing the column, the cystatin E was eluted by 2 M KCl in 25 mM sodium phosphate buffer, pH 6.0. Finally, it was concentrated by ultrafiltration and then dialyzed against PBS. The resulting cystatin E preparation was found to be more than 95% pure by SDS-PAGE and contained<10 EU endotoxin/mg protein.

Example 6

N-terminal Sequence Analysis

The N-terminal sequence of the CysE recombinant product purified in Example 5, above, was determined as follows. The purified recombinant cystatin E was electrophoresed in SDS polyacrylamide gels (Novex 4–20% gels) and trans-blotted onto a ProBlott membrane (Applied Biosystems, Inc. (ABI)). After staining with Ponceau S (0.2% in 4% acetic acid), the band of interest was excised, placed in a "Blot Cartridge", and subjected to N-terminal amino acid sequence analysis using a model ABI-494 sequencer (Perkin-Elmer-Applied Biosystems, Inc.) and the Gas-phase Blot cycles, according to the manufacturer's instructions.

Alternatively, natural proteins in mixtures were separated by agarose gel electrophoresis, transferred to a polyvinyldifluoride membrane, and N-terminal sequencing was carried out on the individual protein bands using an Applied Biosystems 477A sequencer (Matsudaira, J. Biol. Chem., 262:10035–38 (1987)), according to the manufacturer's instructions.

Example 7

Production and Use of an Antiserum Against Cystatin E

An antiserum against cystatin E was raised by injecting 0.2 mg isolated recombinant antigen (above) in Freund's complete adjuvant (Difco Laboratories) subcutaneously into a rabbit. The injection was repeated after three weeks and the rabbit was bled every third week. The specificity of the antiserum was tested by crossed and classical immunoelectrophoresis of the recombinant cystatin E used as starting material and of concentrated proteinuria urine containing cystatins A, B, C, S, SN and kininogen (Abrahamson et al., J. Biol. Chem. 261:11282–89 (1986), incorporated herein by reference). The IgG fraction of 100 ml antiserum was isolated by absorption to protein A-Sepharose column (Pharmacia-LKB, Uppsala, Sweden) and subsequent elution with a glycine buffer at pH 2.2, according to the manufacturer's instructions.

The IgG fraction was coupled to MiniLeak resin (Kem-En-Tec, Copenhagen, Denmark) as described by the manufacturer, for use in purification of CysE from human fluid and tissue, below.

Example 8

Purification of Cystatin E from Human Urine

Urine from one single individual with mixed glomerular-tubular proteinuria was used as starting material as a source of CysE in the present purification procedure. A sample of 2000 ml urine, supplemented with a protease inhibitor cocktail at the time of collection (to achieve final concentrations of at least 6 mM benzamidinium chloride, 30 mM EDTA, 50 mM Tris and 15 mM sodium azide), was concentrated 20 times by pressure ultrafiltration using a C-DAK artificial kidney with a retention limit of approximately 1,500 Da (Cordia Dow Corp., Miami, Fla.) and stored at −20° C. The sample was mixed with an equal volume of 0.1 M Tris buffer, pH 7.4, containing 0.5 M NaCl, 5 mM benzamidinium chloride, 10 mM EDTA and 0.015 M sodium azide.

The resulting solution was applied to the MiniLeak immunoaffinity resin prepared above packed in a column according to the manufacturer's instructions. After extensive washing of the column with a 0.1 M Tris buffer, pH 7.4, containing 0.5 M NaCl, 5 mM benzamidinium chloride, 10 mM EDTA and 0.015 M sodium azide, a 0.2 M glycine buffer, pH 2.2, with 0.5 M NaCl, 5 mM benzamidinium chloride, 10 mM EDTA, and 0.015 M sodium azide was used to elute immunosorbed proteins. The protein-containing acid effluent was immediately neutralized by addition of 2 M Tris buffer, pH 8.6, and then concentrated to about 100 ml by ultrafiltration using Centricon-3 and Microcon-3 concentrators (Amicon Corp., Danvers, Mass.).

A major, immunoreactive protein band in the effluent was identified after agarose gel electrophoresis and immunofixation. The agarose gel electrophoresis was repeated but the fixation and staining procedure was replaced by blotting of the separated proteins onto a polyvinyldifluoride membrane followed by N-terminal sequencing according to the method described in Example 6, above.

Example 9

Glycosylation Analyses

Cystatin E was analyzed for glycosylation by determining the monosaccharide content in a purified preparation of the recombinant protein. About 10 mg of the protein is hydrolyzed with trifluoroacetic acid and the resulting monosaccharides separated and quantitated on a Dionex carbohydrate analyzer with a PA-1 column and pulsed amperometric detector (Hardy and Townsend, *Methods Enzymol.*, 230:208–225 (1994)). Purified preparations of recombinant and natural cystatin E is characterized by SDS-polyacrylamide electrophoresis after reduction in 15% or 16.5% gels with the buffer systems described by Laemmli, *Nature*, 227:680–85 (1970), and Schgger and von Jagow, *Anal. Biochem.*, 166:368–379 (1979), respectively, and by agarose gel electrophoresis at pH 8.6 (Jeppson et al., *Clin. Chem.*, 25:629–638 (1979)).

Example 10

Enzyme Inhibition Assays

The methods used for active site titration of papain, titration of the molar enzyme inhibitory concentration in cystatin E preparations, and for determination of equilibrium constants for dissociation (Ki) of complexes between cystatin E and cysteine peptidases are described in detail in Hall et al., *Biochem. J.*, 291:123–29 (1993) and Abrahamson, *Methods Enzymol.*, 244:685–700 (1994), both of which are hereby incorporated herein by reference. The enzymes used for equilibrium assays were papain (EC 3.4.22.2; from Sigma, St Louis, Mo.) and cathepsin B (EC 3.4.22.1; from Calbiochem, La Jolla, Calif.). The fluorogenic substrate used was Z-Phe-Arg-NHMec (10 mM; from Bachem Feinchemikalien, Bubendorf, Switzerland) and the assay buffer was 100 mM Na-phosphate buffer (pH 6.5 and 6.0 for papain and cathepsin B, respectively), containing 1 mM dithiothreitol and 2 mM EDTA. Steady state velocities were measured and Ki values were calculated according to Henderson, *Biochem J.*, 127:321–333 (1972), incorporated herein by reference. Corrections for substrate competition were made using Km values of 150=B5M for cathepsins B (Barrett and Kirschke, *Methods Enzymol.*, 80:535–561 (1981) and 60=B5M for papain (Hall et al., Biochem. J., 291:123–29 (1992)), both of which are hereby incorporated herein by reference.

SEQUENCE LISTING

<160> NUMBER OF SEQ ID NOS: 13

<210> SEQ ID NO 1
<211> LENGTH: 588
<212> TYPE: DNA
<213> ORGANISM: Homo sapiens
<220> FEATURE:
<221> NAME/KEY: CDS
<222> LOCATION: (19)..(468)
<223> OTHER INFORMATION:

<400> SEQUENCE: 1

```
ccgacggcac tgacggcc atg gcg cgt tcg aac ctc ccg ctg gcg ctg ggc        51
                    Met Ala Arg Ser Asn Leu Pro Leu Ala Leu Gly
                     1               5                      10 ctg gcc ctg gtc gca ttc tgc ctc ctg gcg ctg cca cgc gat gcc cgg        99
Leu Ala Leu Val Ala Phe Cys Leu Leu Ala Leu Pro Arg Asp Ala Arg
            15                  20                  25 gcc cgg ccg cag gag cgc atg gtc gga gaa ctc cgg gac ctg tcg ccc       147
Ala Arg Pro Gln Glu Arg Met Val Gly Glu Leu Arg Asp Leu Ser Pro
        30                  35                  40
```

```
gac gac ccg cag gtg cag aag gcg gcg cag gcg gcc gtg gcc agc tac    195
Asp Asp Pro Gln Val Gln Lys Ala Ala Gln Ala Ala Val Ala Ser Tyr
 45                  50                  55 aac atg ggc agc aac agc atc tac tac ttc cga gac acg cac atc atc    243
Asn Met Gly Ser Asn Ser Ile Tyr Tyr Phe Arg Asp Thr His Ile Ile
 60                  65                  70                  75 aag gcg cag agc cag ctg gtg gcc ggc atc aag tac ttc ctg acg atg    291
Lys Ala Gln Ser Gln Leu Val Ala Gly Ile Lys Tyr Phe Leu Thr Met
                 80                  85                  90 gag atg ggg agc aca gac tgc cgc aag acc agg gtc act gga gac cac    339
Glu Met Gly Ser Thr Asp Cys Arg Lys Thr Arg Val Thr Gly Asp His
             95                 100                 105 gtc gac ctc acc act tgc ccc ctg gca gca ggg gcg cag cag gag aag    387
Val Asp Leu Thr Thr Cys Pro Leu Ala Ala Gly Ala Gln Gln Glu Lys
         110                 115                 120 ctg cgc tgt gac ttt gag gtc ctt gtg gtt ccc tgg cag aac tcc tct    435
Leu Arg Cys Asp Phe Glu Val Leu Val Val Pro Trp Gln Asn Ser Ser
     125                 130                 135 cag ctc cta aag cac aac tgt gtg cag atg tga taagtccccg agggcgaagg    488
Gln Leu Leu Lys His Asn Cys Val Gln Met
140                 145 ccattgggtt tggggccatg gtggagggca cttcacgtcc gtgggccgta tctgtcacaa    548
taaatggcca gtgctgcttc ttgcaaaaaa aaaaaaaaaa                          588

<210> SEQ ID NO 2
<211> LENGTH: 149
<212> TYPE: PRT
<213> ORGANISM: Homo sapiens

<400> SEQUENCE: 2

Met Ala Arg Ser Asn Leu Pro Leu Ala Leu Gly Leu Ala Leu Val Ala
 1               5                  10                  15

Phe Cys Leu Leu Ala Leu Pro Arg Asp Ala Arg Ala Arg Pro Gln Glu
                 20                  25                  30

Arg Met Val Gly Glu Leu Arg Asp Leu Ser Pro Asp Asp Pro Gln Val
             35                  40                  45

Gln Lys Ala Ala Gln Ala Ala Val Ala Ser Tyr Asn Met Gly Ser Asn
 50                  55                  60

Ser Ile Tyr Tyr Phe Arg Asp Thr His Ile Ile Lys Ala Gln Ser Gln
 65                  70                  75                  80

Leu Val Ala Gly Ile Lys Tyr Phe Leu Thr Met Glu Met Gly Ser Thr
                 85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
        115                 120                 125

Glu Val Leu Val Val Pro Trp Gln Asn Ser Ser Gln Leu Leu Lys His
    130                 135                 140

Asn Cys Val Gln Met
145

<210> SEQ ID NO 3
<211> LENGTH: 146
<212> TYPE: PRT
<213> ORGANISM: Homo sapiens

<400> SEQUENCE: 3

Met Ala Gly Pro Leu Arg Ala Pro Leu Leu Leu Leu Ala Ile Leu Ala
```

-continued

```
1               5                  10                 15
Val Ala Leu Ala Val Ser Pro Ala Gly Ser Ser Pro Lys Pro
                20                 25                 30

Pro Arg Leu Val Gly Pro Met Asp Ala Ser Val Glu Glu Gly
        35                 40                 45

Val Arg Arg Ala Leu Asp Phe Ala Val Gly Glu Tyr Asn Lys Ala Ser
    50                 55                 60

Asn Asp Met Tyr His Ser Arg Ala Leu Gln Val Val Arg Ala Arg Lys
65                  70                 75                  80

Gln Ile Val Ala Gly Val Asn Tyr Phe Leu Asp Val Glu Leu Gly Arg
                85                 90                 95

Thr Thr Cys Thr Lys Thr Gln Pro Asn Leu Asp Asn Cys Pro Phe His
                100                105                110

Asp Gln Pro His Leu Lys Arg Lys Ala Phe Cys Ser Phe Gln Ile Tyr
            115                120                125

Ala Val Pro Trp Gln Gly Thr Met Thr Leu Ser Lys Ser Thr Cys Gln
        130                135                140

Asp Ala
145

<210> SEQ ID NO 4
<211> LENGTH: 142
<212> TYPE: PRT
<213> ORGANISM: Homo sapiens

<400> SEQUENCE: 4

Met Met Trp Pro Met His Thr Pro Leu Leu Leu Thr Ala Leu Met
1               5                  10                 15

Val Ala Val Ala Gly Ser Ala Ser Ala Gln Ser Arg Thr Leu Ala Gly
                20                 25                 30

Gly Ile His Ala Thr Asp Leu Asn Asp Lys Ser Val Gln Arg Ala Leu
            35                 40                 45

Asp Phe Ala Ile Ser Glu Tyr Asn Lys Val Ile Asn Lys Asp Glu Tyr
        50                 55                 60

Tyr Ser Arg Pro Leu Gln Val Met Ala Ala Tyr Gln Gln Ile Val Gly
65                  70                 75                  80

Gly Val Asn Tyr Tyr Phe Asn Val Lys Phe Gly Arg Thr Thr Cys Thr
                85                 90                 95

Lys Ser Gln Pro Asn Leu Asp Asn Cys Pro Phe Asn Asp Gln Pro Lys
            100                105                110

Leu Lys Glu Glu Glu Phe Cys Ser Phe Gln Ile Asn Glu Val Pro Trp
        115                120                125

Glu Asp Lys Ile Ser Ile Leu Asn Tyr Lys Cys Arg Lys Val
    130                135                140

<210> SEQ ID NO 5
<211> LENGTH: 141
<212> TYPE: PRT
<213> ORGANISM: Homo sapiens

<400> SEQUENCE: 5

Met Ala Arg Pro Leu Cys Thr Leu Leu Leu Leu Met Ala Thr Leu Ala
1               5                  10                 15

Gly Ala Leu Ala Ser Ser Ser Lys Glu Glu Asn Arg Ile Ile Pro Gly
                20                 25                 30

Gly Ile Tyr Asp Ala Asp Leu Asn Asp Glu Trp Val Gln Arg Ala Leu
```

-continued

```
                35                  40                  45
His Phe Ala Ile Ser Glu Tyr Asn Lys Ala Thr Glu Asp Glu Tyr Tyr
         50                  55                  60

Arg Arg Pro Leu Gln Val Leu Arg Ala Arg Glu Gln Thr Phe Gly Gly
 65                  70                  75                  80

Val Asn Tyr Phe Phe Asp Val Glu Val Gly Arg Thr Ile Cys Thr Lys
                 85                  90                  95

Ser Gln Pro Asn Leu Asp Thr Cys Ala Phe His Glu Gln Pro Glu Leu
            100                 105                 110

Gln Lys Lys Gln Leu Cys Ser Phe Glu Ile Tyr Glu Val Pro Trp Glu
        115                 120                 125

Asp Arg Met Ser Leu Val Asn Ser Arg Cys Gln Glu Ala
    130                 135                 140

<210> SEQ ID NO 6
<211> LENGTH: 141
<212> TYPE: PRT
<213> ORGANISM: Homo sapiens

<400> SEQUENCE: 6

Met Ala Trp Pro Leu Cys Thr Leu Leu Leu Leu Ala Thr Gln Ala
 1               5                  10                  15

Val Ala Leu Ala Trp Ser Pro Gln Glu Glu Asp Arg Ile Ile Glu Gly
                20                  25                  30

Gly Ile Tyr Asp Ala Asp Leu Asn Asp Glu Arg Val Gln Arg Ala Leu
            35                  40                  45

His Phe Val Ile Ser Glu Tyr Asn Lys Ala Thr Glu Asp Glu Tyr Tyr
         50                  55                  60

Arg Arg Leu Leu Arg Val Leu Arg Ala Arg Glu Gln Ile Val Gly Gly
 65                  70                  75                  80

Val Asn Tyr Phe Phe Asp Ile Glu Val Gly Arg Thr Ile Cys Thr Lys
                 85                  90                  95

Ser Gln Pro Asn Leu Asp Thr Cys Ala Phe His Glu Gln Pro Glu Leu
            100                 105                 110

Gln Lys Lys Gln Leu Cys Ser Phe Gln Ile Tyr Glu Val Pro Trp Glu
        115                 120                 125

Asp Arg Met Ser Leu Val Asn Ser Arg Cys Gln Glu Ala
    130                 135                 140

<210> SEQ ID NO 7
<211> LENGTH: 141
<212> TYPE: PRT
<213> ORGANISM: Homo sapiens

<400> SEQUENCE: 7

Met Ala Gln His Leu Ser Thr Leu Leu Leu Leu Ala Thr Leu Ala
 1               5                  10                  15

Val Ala Leu Ala Trp Ser Pro Lys Glu Glu Asp Arg Ile Ile Pro Gly
                20                  25                  30

Gly Ile Tyr Asn Ala Asp Leu Asn Asp Glu Trp Val Gln Arg Ala Leu
            35                  40                  45

His Phe Ala Ile Ser Glu Tyr Asn Lys Ala Thr Lys Asp Asp Tyr Tyr
         50                  55                  60

Arg Arg Pro Leu Arg Val Leu Arg Ala Arg Gln Gln Thr Val Gly Gly
 65                  70                  75                  80

Val Asn Tyr Phe Phe Asp Val Glu Val Gly Arg Thr Ile Cys Thr Lys
```

```
                        85                  90                  95
Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
        115                 120                 125

Asn Arg Arg Ser Leu Val Lys Ser Arg Cys Gln Glu Ser
    130                 135                 140

<210> SEQ ID NO 8
<211> LENGTH: 32
<212> TYPE: DNA
<213> ORGANISM: Artificial sequence
<220> FEATURE:
<223> OTHER INFORMATION: m-CysE 3' primer

<400> SEQUENCE: 8
cgcggatcct cacatctgca aaagttggc tt                                32

<210> SEQ ID NO 9
<211> LENGTH: 27
<212> TYPE: PRT
<213> ORGANISM: Artificial sequence
<220> FEATURE:
<223> OTHER INFORMATION: A 27 amino acid C-terminal fusion product
      encoded by the pA2 vector

<400> SEQUENCE: 9

Pro Thr Phe Cys Arg Cys Glu Asp Pro Thr Arg Glu Ser Arg Lys Asp
1               5                   10                  15

Leu Arg Tyr Arg Ser Arg His Asp Lys Ile His
            20                  25

<210> SEQ ID NO 10
<211> LENGTH: 26
<212> TYPE: DNA
<213> ORGANISM: Artificial sequence
<220> FEATURE:
<223> OTHER INFORMATION: Contains an NcoI restriction enzyme site

<400> SEQUENCE: 10
cgcccatggc ccggccgcag gagcgc                                      26

<210> SEQ ID NO 11
<211> LENGTH: 26
<212> TYPE: DNA
<213> ORGANISM: Artificial sequence
<220> FEATURE:
<223> OTHER INFORMATION: Contains complementary sequences to a HindIII
      site

<400> SEQUENCE: 11
cgcaagcttg aatggccttc gccctc                                      26

<210> SEQ ID NO 12
<211> LENGTH: 33
<212> TYPE: DNA
<213> ORGANISM: Artificial sequence
<220> FEATURE:
<223> OTHER INFORMATION: Contains a BamHI restriction enzyme site
      followed by an efficient signal for the initiation of translation
      in eukaryotic cells (Kozak, M., J. Mol. Biol., 196:947-950 (1987))

<400> SEQUENCE: 12
cgcggatccg ccatcatggc gcgttcgaac ctc                              33
```

```
<210> SEQ ID NO 13
<211> LENGTH: 26
<212> TYPE: DNA
<213> ORGANISM: Artificial sequence
<220> FEATURE:
<223> OTHER INFORMATION: Contains the cleavage site for the restriction
      endonuclease Asp718

<400> SEQUENCE: 13
cgcggtaccg aatggccttc gccctc                                          26
```

What is claimed is:

1. An isolated polynucleotide comprising a nucleotide sequence encoding a polypeptide having a first amino acid sequence 90% or more identical to a second amino acid sequence selected from the group consisting of:
   (a) amino acid residues 1–149 of SEQ ID NO:2;
   (b) amino acid residues 29–149 of SEQ ID NO:2;
   (c) the amino acid sequence of the full-length polypeptide encoded by the cDNA clone contained in ATCC® Deposit No. 97156; and
   (d) the amino acid sequence of the mature polypeptide encoded by the cDNA clone contained in ATCC® Deposit No. 97156;
   wherein the polypeptide has cysteine protease inhibitor activity.

2. The isolated polynucleotide of claim 1 wherein said second amino acid sequence is (a).

3. The isolated polynucleotide of claim 1 wherein said second amino acid sequence is (b).

4. The isolated polynucleotide of claim 1 wherein said second amino acid sequence is (c).

5. The isolated polynucleotide of claim 1 wherein said second amino acid sequence is (d).

6. The isolated polynucleotide of claim 1 wherein said first amino acid sequence is 95% or more identical to said second amino acid sequence (a).

7. The isolated polynucleotide of claim 1 wherein said first amino acid sequence is 95% or more identical to said second amino acid sequence (b).

8. The isolated polynucleotide of claim 1 wherein said first amino acid sequence is 95% or more identical to said second amino acid sequence (c).

9. The isolated polynucleotide of claim 1 wherein said first amino acid sequence is 95% or more identical to said second amino acid sequence (d).

10. The polynucleotide of claim 1 wherein the polynucleotide further comprises a heterologous polynucleotide sequence.

11. The polynucleotide of claim 10 wherein said heterologous polynucleotide sequence encodes a heterologous polypeptide.

12. A recombinant vector comprising the polynucleotide of claim 1.

13. The recombinant vector of claim 12 wherein the polynucleotide is operably associated with a heterologous regulatory sequence that controls gene expression.

14. A method of producing a recombinant vector comprising inserting the isolated polynucleotide of claim 1 into a vector.

15. A recombinant host cell comprising the isolated polynucleotide of claim 1.

16. A recombinant host cell of claim 15 wherein the polynucleotide is operably associated with a heterologous regulatory sequence that controls gene expression.

17. A recombinant host cell comprising the recombinant vector of claim 12.

18. A method of producing a host cell comprising transducing, transforming, or transfecting a host cell with the vector of claim 12.

19. A method for producing a polypeptide, comprising:
   (a) culturing the host cell of claim 16 under conditions suitable to produce a polypeptide encoded by said polynucleotide; and
   (b) recovering said polypeptide.

20. A composition comprising the polynucleotide of claim 1 and a carrier.

21. An isolated polynucleotide consisting of at least 30 contiguous nucleotides of SEQ ID NO:1, or the complementary strand thereto.

22. The isolated polynucleotide of claim 21 wherein said polynucleotide consists of at least 30 contiguous nucleotides of SEQ ID NO:1.

23. The isolated polynucleotide of claim 21 wherein said polynucleotide consists of at least 30 contiguous nucleotides of the complementary strand of SEQ ID NO:1.

24. The isolated polynucleotide of claim 21 wherein said polynucleotide consists of at least 50 contiguous nucleotides of SEQ ID NO:1.

25. The isolated polynucleotide of claim 21 wherein said polynucleotide consists of at least 50 contiguous nucleotides of the complementary strand of SEQ ID NO:1.

26. The isolated polynucleotide of claim 21 wherein said polynucleotide consists of nucleotides 19 to 465 of SEQ ID NO:1.

27. The isolated polynucleotide of claim 21 wherein said polynucleotide consists of nucleotides 102 to 465 of SEQ ID NO:1.

28. The isolated polynucleotide of claim 21 wherein said polynucleotide consists of nucleotides 1 to 588 of SEQ ID NO:1.

29. The polynucleotide of claim 21 wherein the polynucleotide further comprises a heterologous polynucleotide sequence.

30. The polynucleotide of claim 29 wherein said heterologous polynucleotide sequence encodes a heterologous polypeptide.

31. A recombinant vector comprising the polynucleotide of claim 21.

32. The recombinant vector of claim 31 wherein the polynucleotide is operably associated with a heterologous regulatory sequence that controls gene expression.

33. A method of producing a recombinant vector comprising inserting the isolated polynucleotide of claim 21 into a vector.

34. A recombinant host cell comprising the isolated polynucleotide of claim 21.

35. The recombinant host cell of claim 34 wherein the polynucleotide is operably associated with a heterologous regulatory sequence that controls gene expression.

36. A recombinant host cell comprising the recombinant vector of claim 31.

37. A method of producing a host cell comprising transducing, transforming or transfecting a host cell with the vector of claim 31.

38. A method for producing a polypeptide, comprising:
(a) culturing the host cell of claim 35 under conditions suitable to produce a polypeptide encoded by said polynucleotide; and
(b) recovering said polypeptide.

39. A composition comprising the polynucleotide of claim 21 and a carrier.

40. An isolated polynucleotide consisting of at least 30 contiguous nucleotides of the cDNA contained in ATCC® Deposit No. 97156, or the complementary strand thereto.

41. The isolated polynucleotide of claim 40 wherein said polynucleotide consists of at least 30 contiguous nucleotides of the cDNA contained in ATCC® Deposit No. 97156.

42. The isolated polynucleotide of claim 40 wherein said polynucleotide consists of at least 30 contiguous nucleotides of the complementary strand of the cDNA contained in ATCC® Deposit No. 97156.

43. The isolated polynucleotide of claim 40 wherein said polynucleotide consists of at least 50 contiguous nucleotides of the cDNA contained in ATCC® Deposit No. 97156.

44. The isolated polynucleotide of claim 40 wherein said polynucleotide consists of at least 50 contiguous nucleotides of the complementary strand of the cDNA contained in ATCC® Deposit No. 97156.

45. The isolated polynucleotide of claim 40 wherein said polynucleotide consists of the cDNA contained in ATCC® Deposit No. 97156.

46. The isolated polynucleotide of claim 40 wherein said polynucleotide consists of the complementary strand of the cDNA contained in ATCC® Deposit No. 97156.

47. The polynucleotide of claim 40 wherein the polynucleotide further comprises a heterologous polynucleotide sequence.

48. The polynucleotide of claim 47 wherein said heterologous polynucleotide sequence encodes a heterologous polypeptide.

49. A recombinant vector comprising the polynucleotide of claim 40.

50. The recombinant vector of claim 49 wherein the polynucleotide is operably associated with a heterologous regulatory sequence that controls gene expression.

51. A method of producing a recombinant vector comprising inserting the isolated polynucleotide of claim 40 into a vector.

52. A recombinant host cell comprising the isolated polynucleotide of claim 40.

53. The recombinant host cell of claim 52 wherein the polynucleotide is operably associated with a heterologous regulatory sequence that controls gene expression.

54. A recombinant host cell comprising the recombinant vector of claim 49.

55. A method of producing a host cell comprising transducing, transforming or transfecting a host cell with the vector of claim 49.

56. A method for producing a polypeptide, comprising:
(a) culturing the host cell of claim 53 under conditions suitable to produce a polypeptide encoded by said polynucleotide; and
(b) recovering said polypeptide.

57. A composition comprising the polynucleotide of claim 40 and a carrier.

58. An isolated polynucleotide comprising a nucleotide sequence encoding the amino acid sequence of the full-length polypeptide encoded by the cDNA clone contained in ATCC® Deposit No. 97156.

59. The polynucleotide of claim 58 wherein the polynucleotide further comprises a heterologous polynucleotide sequence.

60. The polynucleotide of claim 59 wherein said heterologous polynucleotide sequence encodes a heterologous polypeptide.

61. A recombinant vector comprising the polynucleotide of claim 58.

62. The recombinant vector of claim 61 wherein the polynucleotide is operably associated with a heterologous regulatory sequence that controls gene expression.

63. A method of producing a recombinant vector comprising inserting the isolated polynucleotide of claim 58 into a vector.

64. A recombinant host cell comprising the isolated polynucleotide of claim 58.

65. The recombinant host cell of claim 64 wherein the polynucleotide is operably associated with a heterologous regulatory sequence that controls gene expression.

66. A recombinant host cell comprising the recombinant vector of claim 61.

67. A method of producing a host cell comprising transducing, transforming or transfecting a host cell with the vector of claim 61.

68. A method for producing a polypeptide, comprising:
(a) culturing the host cell of claim 65 under conditions suitable to produce a polypeptide encoded by said polynucleotide; and
(b) recovering said polypeptide.

69. A composition comprising the polynucleotide of claim 58 and a carrier.

* * * * *